United States Patent
Graumann et al.

(10) Patent No.: US 6,811,313 B2
(45) Date of Patent: Nov. 2, 2004

(54) C-ARM X-RAY SYSTEM WITH ADJUSTABLE DETECTOR POSITIONING

(75) Inventors: Rainer Graumann, Hoechstadt (DE); Oliver Schuetz, Erlangen (DE); Norbert Strobel, Baiersdorf (DE)

(73) Assignee: Siemens Aktiengesellschaft, München (DE)

( * ) Notice: Subject to any disclaimer, the term of this patent is extended or adjusted under 35 U.S.C. 154(b) by 121 days.

(21) Appl. No.: 10/253,675

(22) Filed: Sep. 24, 2002

(65) Prior Publication Data

US 2003/0058996 A1 Mar. 27, 2003

(30) Foreign Application Priority Data

Sep. 25, 2001 (DE) .......................................... 101 47 160

(51) Int. Cl.[7] ................................................ H05G 1/02
(52) U.S. Cl. ........................................ 378/196; 378/167
(58) Field of Search ................................. 378/196, 197, 378/198, 167

(56) References Cited

U.S. PATENT DOCUMENTS 6,412,978 B1 * 7/2002 Watanabe et al. ........... 378/197

* cited by examiner

Primary Examiner—Edward J. Glick
Assistant Examiner—Courtney Thomas
(74) Attorney, Agent, or Firm—Schiff Hardin LLP

(57) ABSTRACT

A C-arm X-ray system has a C-arm that carries an X-ray source and a detector opposite one another at its ends and that can be swiveled around the subject in multiple axes. The detector is mounted so as to be rotatable around the proceeding axis therefrom to the X-ray source and/or to be displaceable parallel to the detector surface and/or along a arcuate path.

6 Claims, 1 Drawing Sheet

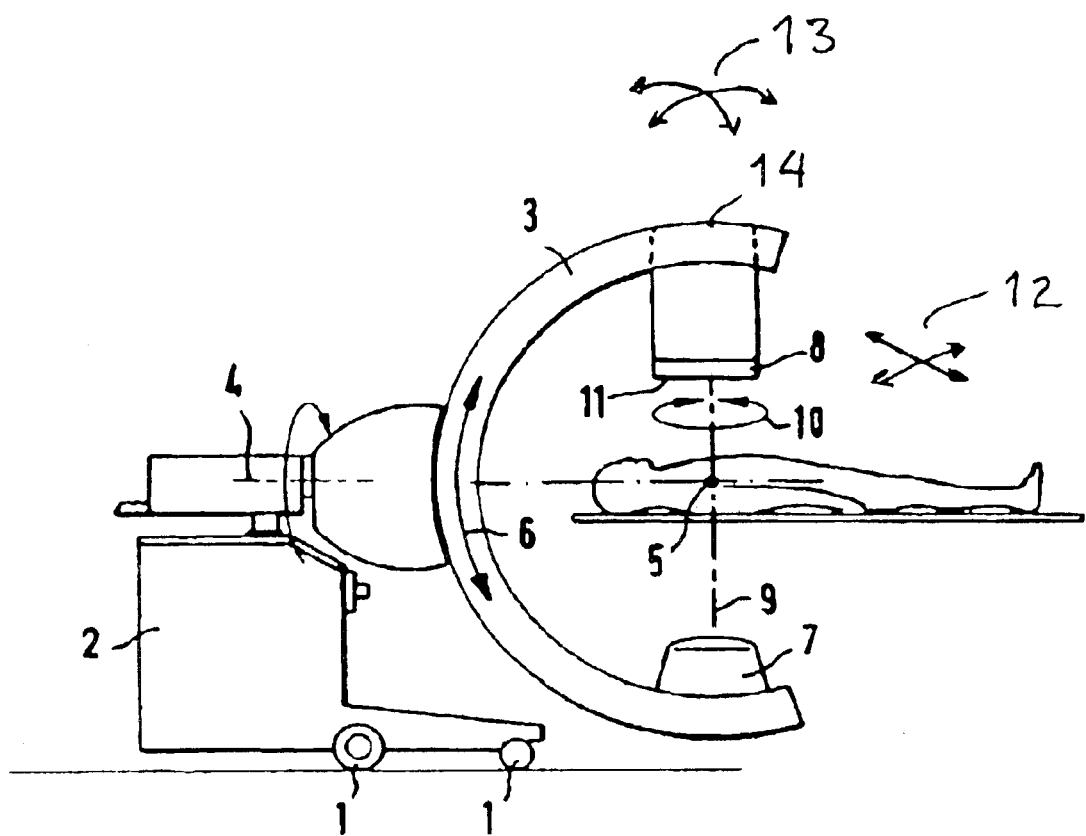

C-ARM X-RAY SYSTEM WITH ADJUSTABLE DETECTOR POSITIONING

BACKGROUND OF THE INVENTION

1. Field of the Invention

The present invention is directed to a C-arm X-ray system having a C-arm that carries an X-ray source and a detector residing opposite one another at its ends, and that can be swiveled around the subject in multiple axes.

2. Description of the Prior Art

In addition to the swivel of the C-arm around an axis lying essentially horizontally in the plane of the C-arm—angulation—, the C-arm also can swivel in its plane around an axis perpendicular thereto—referred to as orbital rotation.

Due to the properties of the commonly employed Feldkamp image reconstruction algorithm, only that part of a volume that is covered in each 2D projection in a graduated circle revolution can be calculated. Since the reconstruction algorithm is based on the principle of filtered back-projection, projections that are cut off in the filter direction should be avoided. For calculating thorax slices, for example, it is therefore necessary to employ a detector with dimensions large enough in one dimension (length) so as to completely cover the full width of the trunk of the body. The height of the detector determines how many axial slices can be calculated.

In practice, the reoccurring problem arises that, due to the detector residing stationarily opposite the X-ray source and with a limited positioning possibilities of the C-arm, projections that are more or less cut off and that negatively influence the reconstruction result are generated dependent on the subject position and the rotational sense. Moreover, volumes of different sizes are obtained, their size being dependent on whether an angulation or an orbital rotation is implemented. When the objective is for the subject to be imaged to be largely completely covered in the projection exposures in all rotational directions, then a quadratic detector must be employed, that may be unnecessarily large and that is correspondingly expensive.

SUMMARY OF THE INVENTION

An object of the present invention is to design a C-arm X-ray system of the type initially described wherein, despite a limited size of the detector surface, better image qualities can be achieved by avoiding clipped projections.

This object is inventively achieved in a C-arm system wherein the detector is mounted so as to be rotatable around the axis preceding therefrom to the X-ray source and/or to be displaceable parallel to the detector surface and/or along a arcuate path. The detector preferably has a rectangular detector surface and is pivotable by at least 90° such that the long side can be aligned parallel to the rotational plane. Given an angulation, thus, the long side of the rectangular detector surface resides perpendicular to the plane of the C-arm, and, given orbital rotation, the long side of the detector surface lies parallel to the plane of the C-arm.

The displaceability of the detector parallel to the detector surface or along an arcuate path is particularly useful in instances wherein there is no isocenter for the orbital rotation or when the arrangement is undertaken such that a 360° scan is possible.

DESCRIPTION OF THE DRAWING

The single FIGURE is a side view of a C-arm X-ray system constructed and operating in accordance with the principles of the present invention.

DESCRIPTION OF THE PREFERRED EMBODIMENTS

The illustrated C-arm X-ray system is composed of a base frame 2 movable on wheels 1 and at which a C-arm 3 is seated such that it is rotatable around the axis 4 (angulation) such that it also can be turned around an axis 5 in the direction of the double arrow 6 (orbital rotation). An X-ray source 7 and a detector 8, preferably a rectangular flat detector, residing 180° opposite one another, are secured to the C-arm 3 in the region of its ends. Inventively, the detector is mounted to the C-arm 3 by a mounting arrangement 14 so as to be either rotatable (double arrow 10) around the axis 9 proceeding to the X-ray source 7—through the isocenter coinciding with the axis 5 in the FIGURE in the illustrated exemplary embodiment—and/or displaceable parallel to the detector surface 11, i.e. parallel to the plane of the C-arm 3 as well as perpendicular to the plane of the C-arm 3 as indicated by arrows 12. Additionally, the detector 8 can be displaced out of its initial position shown in the FIGURE, along an arcuate path. The arcuate path preferably extends along the curvature of the C-arm 3 or intersects the C-arm 3 at a right angle as indicated by the arrows 13. The rotatability around the axis 9—given a rectangular detector—makes it possible to set the long side such dependent on rotational sense that this long side lies parallel to the rotational plane. Clipped projections thus are largely avoided. The potentially additional displaceability of the detector parallel to its detector surface 11 or along an arcuate path—which is not absolutely necessary given the illustrated exemplary embodiment with isocenter—has the same advantage of avoiding clipped projections by means of a suitable displacement dependent on rotational sense given systems without isocenter that enable a 360° scan.

Although modifications and changes may be suggested by those skilled in the art, it is the intention of the inventors to embody within the patent warranted hereon all changes and modifications as reasonably and properly come within the scope of their contribution to the art.

We claim as our invention:

1. A C-arm X-ray system comprising:
   a C-arm having first and second opposite ends;
   an X-ray source mounted at said first end at said C-arm;
   a radiation detector mounted at said second end of said C-arm, said radiation detector having a detector surface opposite said X-ray source, with an axis proceeding between said X-ray source and said radiation detector;
   a holder to which said C-arm is mounted allowing said C-arm to be rotated around a subject in a plurality of axes; and
   a mounting arrangement for mounting said radiation detector to said second end of said C-arm allowing adjustment of said radiation detector parallel to said detector surface.

2. A C-arm X-ray system as claimed in claim 1 wherein said detector surface is rectangular with a long side, and wherein said mounting arrangement also allows adjustment of said radiation detector so that said detector surface is pivotable by at least 90° with said long side aligned parallel to a rotational plane of the C-arm.

3. A C-arm X-ray system as claimed in claim 2 wherein said radiation detector is a flat detector.

4. A C-arm X-ray system as claimed in claim 1 wherein said mounting arrangement also allows adjustment of said radiation detector around said axis between said radiation detector and said X-ray source.

5. A C-arm X-ray system as claimed in claim 1 wherein said mounting arrangement also allows adjustment of said radiation detector along an arcuate path.

6. A C-arm X-ray system as claimed in claim 1 wherein said mounting arrangement also allows adjustment of said radiation detector around said axis between said radiation detector and said X-ray source, and along an arcuate path.

* * * * *